(12) United States Patent
Child et al.

(10) Patent No.: US 10,272,214 B2
(45) Date of Patent: Apr. 30, 2019

(54) VALVE FOR PRESSURIZED METERED DOSE DISPENSER

(71) Applicant: 3M INNOVATIVE PROPERTIES COMPANY, St. Paul, MN (US)

(72) Inventors: Andrew D Child, Clitheroe (GB); Stephen D Helm, Blackburn (GB)

(73) Assignee: 3M Innovative Properties Company, St. Paul, MN (US)

( * ) Notice: Subject to any disclaimer, the term of this patent is extended or adjusted under 35 U.S.C. 154(b) by 715 days.

(21) Appl. No.: 14/899,020

(22) PCT Filed: Jun. 17, 2014

(86) PCT No.: PCT/US2014/042722
§ 371 (c)(1),
(2) Date: Dec. 16, 2015

(87) PCT Pub. No.: WO2014/204951
PCT Pub. Date: Dec. 24, 2014

(65) Prior Publication Data
US 2016/0121059 A1 May 5, 2016

(30) Foreign Application Priority Data
Jun. 20, 2013 (GB) .................................. 1311034.1

(51) Int. Cl.
*A61M 15/00* (2006.01)
*B65D 83/38* (2006.01)
(Continued)

(52) U.S. Cl.
CPC ........ *A61M 15/002* (2014.02); *A61M 15/009* (2013.01); *B65D 83/38* (2013.01);
(Continued)

(58) Field of Classification Search
CPC .............. A61M 15/0001; A61M 15/00; A61M 15/009; A61M 11/00; B65D 83/54;
(Continued)

(56) References Cited

U.S. PATENT DOCUMENTS 3,130,880 A * 4/1964 Briechle ................ B65D 83/54
222/402.2
3,556,357 A 1/1971 Graham
(Continued)

FOREIGN PATENT DOCUMENTS

DE 9017394 3/1991
GB 1336379 11/1973
(Continued)

OTHER PUBLICATIONS

Extended Search Report for EP 14813066.9 dated Jan. 18, 2017.

*Primary Examiner* — Gregory A Anderson
*Assistant Examiner* — Margaret M Luarca (57) ABSTRACT

A valve for an aerosol canister for containing medicaments is disclosed. The valve comprises a valve assembly, a ferrule for holding the valve assembly and a gasket for insertion into the ferrule. The ferrule has at least one ferrule interference surface and the gasket has at least one gasket interference surface, and the contact zone between the ferrule interference surface and the gasket interference surface comprises a plurality of relief portions. Preferably, the ferrule interference surface comprises a plurality of ferrule relief pockets and the gasket interference surface comprises a plurality of gasket relief pockets. Also disclosed is a method of manufacturing a valve for an aerosol canister.

28 Claims, 5 Drawing Sheets

(51) Int. Cl.
*B65D 83/30* (2006.01)
*B65D 83/54* (2006.01)

(52) U.S. Cl.
CPC ......... *A61M 2207/00* (2013.01); *B65D 83/30* (2013.01); *B65D 83/54* (2013.01)

(58) Field of Classification Search
CPC ........ B65D 83/38; B65D 83/75; B65D 83/40; B65D 21/0219; F16L 19/065
See application file for complete search history.

(56) References Cited

U.S. PATENT DOCUMENTS

| | | |
|---|---|---|
| 4,278,189 A | 7/1981 | Kirk, Jr. |
| 5,484,466 A | 1/1996 | Brown |
| 2003/0031806 A1 | 2/2003 | Jinks |
| 2007/0158369 A1 | 7/2007 | Margheritis et al. |
| 2008/0006657 A1 | 1/2008 | Griemla |
| 2014/0231466 A1 | 8/2014 | Du Boisbaudry et al. |

FOREIGN PATENT DOCUMENTS

| | | |
|---|---|---|
| GB | 2077229 | 12/1981 |
| JP | 2004099180 | 4/2004 |
| WO | 2007107174 | 9/2007 |

\* cited by examiner

VALVE FOR PRESSURIZED METERED DOSE DISPENSER

CROSS REFERENCE TO RELATED APPLICATIONS

This application is a national stage filing under 35 U.S.C. 371 of PCT/US2014/042722, filed Jun. 17, 2014, which claims priority to United Kingdom Application No. GB 1311034.1, filed Jun. 20, 2013, the disclosure of which is incorporated by reference in its/their entirety herein.

BACKGROUND OF THE INVENTION

The present specification relates to valves for aerosol containers, more particularly valves for aerosol containers for containing medicaments. The present specification also relates to aerosol containers having such valves fitted thereto and to methods for manufacturing such valves.

Pressurized metered dose dispensers have been known for over 50 years, particularly inhalers for the treatment of asthma, but also for other diseases where the lung, throat or nasal passages are suitable sites for delivery of drugs. A formulation of drug in such a dispenser is typically either in the form of a suspension or a solution in a propellant system, depending on the solubility of the drug in the formulation.

Medicinal aerosol formulations are often contained in a metal, plastic or glass vial or container equipped with a metered dose valve. The valve may be fitted to the body of the vial by crimping a ferrule, holding a valve assembly, against the body of the vial with an intermediate seal made of an elastomeric material compressed between the body and the ferrule. The intermediate seal can be in the form of a ferrule gasket placed and compressed between the top edge of the body of the vial and the opposing surface of the ferrule gasket, and/or it can be in the form of an O-ring placed around the body of the vial and compressed between the body of the vial and an annular flange of the valve ferrule.

U.S. Pat. No. 3,556,357 relates to closures of aerosol containers of the kind having a valve with a tubular stem passed with clearance through an aperture in the container cap, the stem carrying at its outer end the conventional head and nozzle whereas its inner end is provided with a flange. Two further such designs are disclosed in United Kingdom Patent Nos. 1,336,379 and 2,077,229.

SUMMARY

In some designs of valve, tolerance stack-up may occasionally lead to incorrectly seated or missing gaskets. Such a problem reduces efficiency and/or yield of production and can lead to higher costs and delays on the production line. There is therefore a need to provide for improved location and retention of gaskets in valves, especially during manufacture.

In a first aspect the present invention accordingly provides a valve for an aerosol canister, the valve comprising a valve assembly, a ferrule for holding the valve assembly and a gasket for insertion in the ferrule, wherein the ferrule has at least one ferrule interference surface and the gasket has at least one gasket interference surface, and wherein the contact zone between the ferrule interference surface and the gasket interference surface comprises a plurality of relief portions.

This is advantageous because the relief portions have surprisingly been found to maintain a good interference fit between the gasket and ferrule even with a reduction in average push-fit force, and to reduce the chances of gasket slippage or displacement or loss even when the dimensions of the gasket and/or ferrule are not exactly at their nominal values.

Preferably, the ferrule interference surface comprises a plurality of ferrule relief pockets.

Additionally or alternatively, preferably the gasket interference surface comprises a plurality of gasket relief pockets.

Thus, in a second aspect the present invention provides a valve for an aerosol canister, the valve comprising a valve assembly, a ferrule for holding the valve assembly and a gasket for insertion into the ferrule, wherein the ferrule has at least one ferrule interference surface and the gasket has at least one gasket interference surface, and wherein the ferrule interference surface and/or the gasket interference surface comprise a plurality of relief pockets.

The interference surface of the gasket may be either the inner interference surface (i.e. on the inside of an annular gasket), or the outer interference surface (i.e. on the outside of an annular gasket) or both.

The interference surface of the ferrule may be either the inner interference surface (i.e. to contact the inside of an annular gasket), or the outer interference surface (i.e. to contact the outside of an annular gasket) or both.

Usually, the gasket interference surface and/or the ferrule interference surface will be substantially cylindrical.

Preferably, the relief portions will be distributed substantially evenly over the gasket interference surface. The number of relief pockets may be an even number (e.g. 6, 8, 10, 12, 14, 16, or 18) or an odd number (e.g. 5, 7, 9, 11, 13 or 15). It is preferred that there are five or more gasket relief pockets.

It is preferred if the gasket relief pockets and/or the ferrule relief pockets, where applicable, are distributed substantially evenly on the gasket and/or ferrule interference surface. The number of gasket and/or ferrule relief pockets may be, independently of each other, an even number (e.g. 6, 8, 10, 12, 14 or 16) or an odd number (e.g. 5, 7, 9, 11, 13 or 15). It is preferred that there are five or more gasket and/or ferrule relief pockets.

The profile of the relief pockets may be of generally any suitable shape, for example, (in plan view, and allowing for the curvature of the component) substantially square, substantially rectangular or shaped substantially as part of an oval or circle. From a side view the relief pockets may be of any suitable shape, but substantially square or substantially rectangular profiles are preferred.

The invention is particularly advantageous where the valve is a metered dose aerosol valve. The valve is usually adapted for fitting to an aerosol container and the gasket is for sealing the valve ferrule to the aerosol container.

The gasket may be made from any suitable elastomeric material. The gasket may therefore comprise a thermoset elastomer that may include one or more of thermoset ethylene-propylene-diene terpolymer (EPDM), acrylonitrile-butadiene copolymer (Nitrile rubber), isobutylene-isoprene copolymer (Butyl rubber), halogenated isobutylene-isoprene copolymer (e.g. Chlorobutyl rubber and Bromobutyl rubber), polychloroprene (Neoprene), and mixtures thereof, with EPDM, nitrile rubber and butyl rubber being more preferred, EPDM and nitrile rubber even more preferred and EPDM most preferred. Alternatively or additionally, the gasket may comprise one or more suitable thermoplastic elastomers including one or more of polyester rubbers, polyurethane rubbers, ethylene vinyl acetate rubber, styrene butadiene rubber, copolyester thermoplastic elastomers, copolyester ether thermoplastic elastomers, olefinic thermoplastic elastomers, mixture of inter-dispersed relative hard and relative soft domains of thermoplastics and elastomers (e.g. Santoprene), polyester amide thermoplastic elastomers, polyether amide thermoplastic elastomers, copolyamide thermoplastic elastomers and mixtures thereof.

Generally, the valve assembly will comprise a helical spring, a seal and a valve stem, the valve stem and seal being in mutual sliding sealing engagement, the helical spring comprising a coil of elongate material for returning the valve stem to a rest position.

The relief pockets will usually be recesses in the gasket interference surface or ferrule interference surface.

Preferably, the ferrule relief pockets are recessed by between 0.01 and 5 mm from a substantially cylindrical ferrule interference surface, more preferably by between 0.02 and 2 mm, and most preferably by between 0.03 and 1.8 mm, or 0.1 mm to 1.5 mm. The most preferred ferrule recess is in the range 0.1 mm to 0.5 mm.

Preferably, the gasket relief pockets are recessed by between 0.01 and 5 mm from a substantially cylindrical gasket interference surface, more preferably by between 0.02 and 2.5 mm, and most preferably by between 0.03 and 1.8 mm.

The circumferential width of the ferrule and/or gasket relief pockets are independently selected to be in the range 0.5 mm to 7 mm, more preferably 1 mm to 5 mm and most preferably 1 mm to 4 mm.

In a third aspect there is provided an aerosol container having fitted thereto a valve as in the first aspect. The aerosol canister may contain a medicament aerosol formulation.

Medicinal aerosol formulations may comprise a medicament either in solution or as particles suspended in liquefied propellant(s), e.g. CFC propellant(s) or more usually non-CFC propellant(s) such as 1,1,1,2-tetrafluoroethane (HFA134a) and/or 1,1,1,2,3,3,3-heptafluoropropane (HFA227). If desired and/or deemed necessary, the formulation may comprise one or more other components, such as excipients, co-solvents, e.g. ethanol, and/or suspending aids (e.g. surfactants). Depending on the particular metered dose valve and/or filling system, medicament formulation may be filled into the pMDI either by cold-filling (in which chilled formulation is filled into the vial and subsequently the metered dose valve is fitted onto the vial) or by pressure filling (in which the metered dose valve is fitted onto the vial and then formulation is pressure filled through the valve into the vial).

The medicament may be a drug, vaccine, DNA fragment, hormone or other treatment. The amount of medicament is typically determined by the required dose per puff (actuation) and by available valve sizes, which are typically around 25, 50 or 63 microliters, but may be around 100 microliters where particularly large doses are required.

Suitable drugs include those for the treatment of respiratory disorders, e.g., bronchodilators, anti-inflammatories (e.g. corticosteroids), anti-allergies, anti-asthmatics, anti-histamines, and anti-cholinergic agents. Therapeutic proteins and peptides may be employed for delivery by inhalation.

Exemplary drugs which may be employed for delivery by inhalation include but are not limited to: albuterol (salbutamol), terbutaline, ipratropium, oxitropium, tiotropium, aclidinium, glycopyrrolate, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, vilanterol, olodaterol, milveterol, omalizumab, zileuton, insulin, pentamidine, calcitonin, leuprolide, alpha-1-antitrypsin, interferons, triamcinolone, and pharmaceutically acceptable salts and esters thereof for example albuterol sulfate, aclidinium bromide formoterol fumarate, salmeterol xinafoate, beclomethasone dipropionate, triamcinolone acetonide, fluticasone propionate, fluticasone furoate, vilanterol terfenetate, tiotropium bromide, leuprolide acetate and mometasone furoate.

Medicinal aerosol formulations may comprise excipients other than surfactants or ethanol, such as a particulate bulking agent, which may be in micronized or submicron form. Examples of such excipients include lactose, sucrose, alanine and sodium sulphate. Other propellant components are possible, such as gases or liquids soluble in the HFAs, e.g. $CO_2$.

In a fourth aspect, the invention provides a method of manufacturing a valve for an aerosol canister, the valve comprising a valve assembly, a ferrule for holding the valve assembly and a gasket for insertion in the ferrule, the method comprising providing a ferrule, providing a gasket adapted to fit the ferrule, and inserting the gasket in the ferrule, wherein the ferrule has at least one ferrule interference surface and the gasket has at least one gasket interference surface, and wherein the contact zone between the ferrule interference surface and the gasket interference surface comprises a plurality of relief portions. Preferably, the ferrule interference surface and/or the gasket interference surface comprise a plurality of relief pockets.

BRIEF DESCRIPTION OF THE DRAWINGS

So that the present specification may be more completely understood, reference is made to the accompanying drawings in which:

FIG. 3b shows a section on A-A of the ferrule of FIG. 3a.

FIG. 3c shows a section on F-F of the ferrule of FIG. 3a.

FIG. 4b shows a section on B-B of the gasket of FIG. 4a

FIG. 5b shows a section on D-D of the gasket of FIG. 5a.

DETAILED DESCRIPTION

Figure 1:
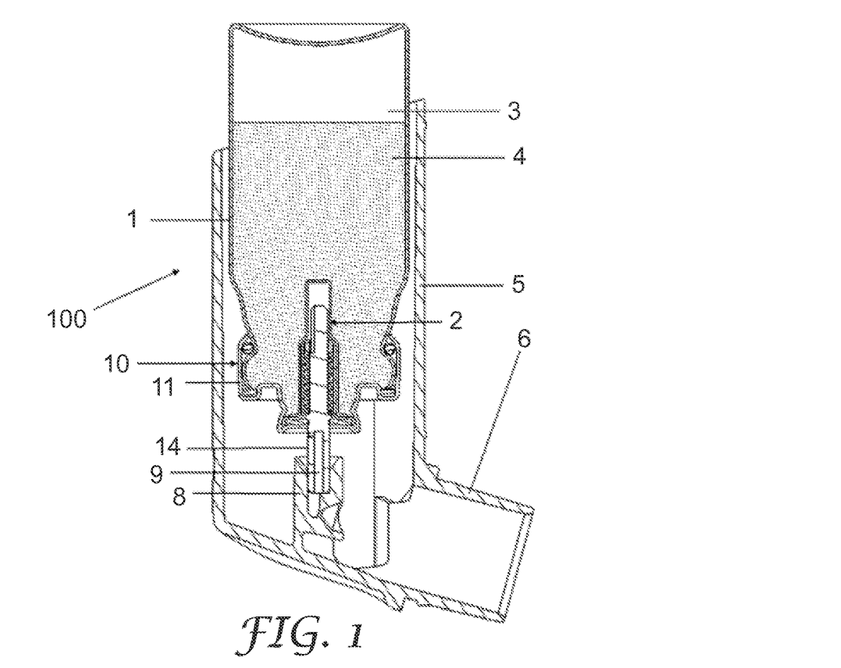
FIG. 1 shows a cross-sectional view of a pressurised metered dose inhaler (pMDI).
Figure 2:
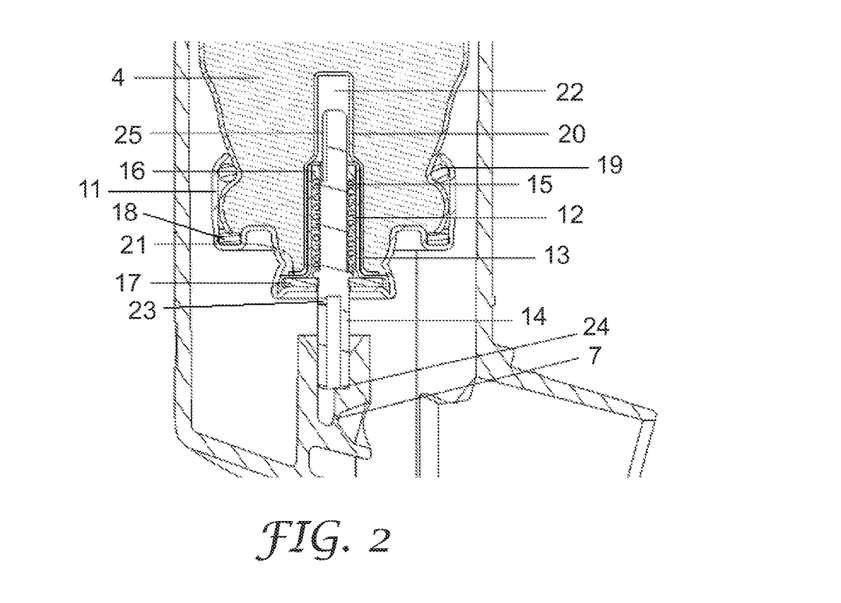
FIG. 2 shows an enlarged partial view of the inhaler shown in FIG. 1.

FIG. 1 shows a pressurised metered dose inhaler (pMDI) 100 comprising a canister 10 including a metered dose-dispensing valve 2 mounted via a ferrule 11 onto an aerosol container or vial 1. FIG. 2 shows a detailed view of the lower part of the pMDI shown in FIG. 1. The container defines, in part, a formulation chamber 3 filled with medicinal inhalation formulation 4 and an actuator 5 including a mouthpiece 6 (in an alternative form, suitable for nasal drug delivery, the actuator may comprise a nosepiece rather than a mouthpiece). The canister 1 is placed within the actuator 5 by inserting the valve stem 14 of the valve 2, which protrudes outside the ferrule 11, into a support block 8 of the actuator 5. The valve stem 14 has a dispensing passage 9 that allows for passage of substance from a metering chamber of the valve 2 out through the valve stem 14 and actuator mouthpiece 6 (or nosepiece) to the user. In operation, medicament formulation 4 can pass from the formulation chamber 3 into a pre-metering region 22 provided between the second valve body 20 housing and the first valve body 13 through an annular space 21 between a flange of the second valve body and the first valve body. To actuate (fire) the valve to deliver a dose of medicament formulation, the valve stem 14 is pushed inwardly relative to the aerosol container from its resting position shown in FIGS. 1 and 2, allowing formulation to pass from the metering chamber 12 through a side hole 23 in the valve stem 14 and through a stem outlet 24 out through an actuator nozzle 7 and then out to the patient. When the valve stem 14 is released, medicament formulation enters into the valve, in particular into the pre-metering chamber 22, through the annular space 21 and thence from the pre-metering chamber 22 through a groove 25 in the valve stem 14 past the inner seal 16 into the metering chamber 12. Because such valves retain the next dose of medication formulation in the metering chamber 12 between actuations, they are sometimes referred to as "retention valves".

A first valve body 13 defines in part a metering chamber 12, a second valve body 20 defines in part a pre-metering region 22 and acts in this valve as a bottle emptier, a valve stem 14, a biasing member in the form of a coil spring 15, an inner seal 16, an outer seal 17, a ferrule 11 and a gasket 18. A further seal may optionally be formed by an O-ring 19.

Figure 3A:
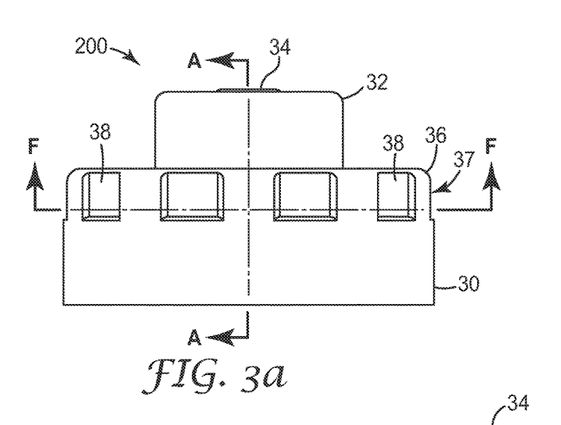
FIG. 3a shows a side view of a ferrule for incorporation in valves of the invention.

FIG. 3a shows a side view of a castellated ferrule 200 for incorporation into the valves of the invention. The ferrule 200 has a skirt 30 of cylindrical form. The skirt 30 is intended to be crimped on to the neck of a canister (not shown in FIG. 3; see FIG. 1 or 2). Above the skirt 30 (in the orientation shown in FIG. 3a), a valve portion 32 of smaller diameter is formed integrally with the skirt 30. The valve portion 32 contains the valve stem opening 34 through which the valve stem of the valve is inserted when the valve is assembled. Between the skirt 30 and the valve portion 32, the gasket portion 36 of the ferrule 200 has a number of recesses 38 stamped into the outer surface 37 of the gasket portion 36 and evenly spaced around the circumference of the ferrule 200.

Figure 3B:
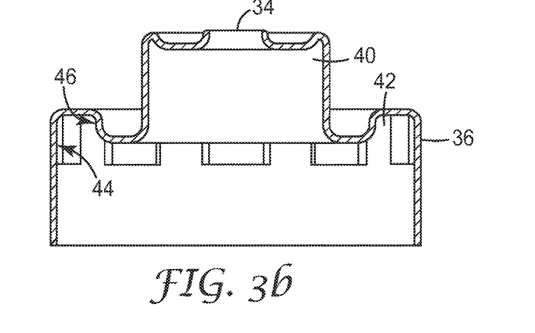
Figure 3C:
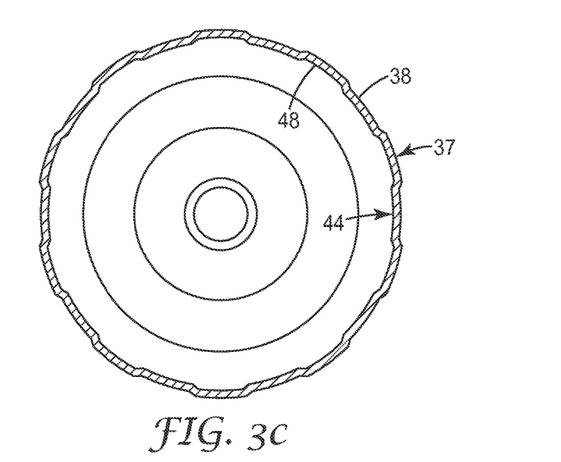

FIGS. 3b and 3c show other perspectives of the castellated ferrule 200 shown in FIG. 3a. The ferrule 200 is a hollow body with an outer seal volume 40 situated below the valve stem opening 34. In the interior of the gasket portion 36, there is a gasket volume 42 that is for holding and retaining a gasket. The gasket volume 42 is adapted to hold the gasket between the outer interference surface 44 and inner interference surface 46. The recesses 38 stamped into the outer surface 37 of the gasket portion 36 form a castellated profile, giving relief pockets 48 on the outer interference surface 44. When a gasket is inserted into the gasket volume 42 it is generally held in place by interference with the inner interference surface 46 and outer interference surface 44. The relief pockets 48 reduce the push fit force to insert the gasket but improve retention of the gasket in the ferrule 200 thereby leading to important production advantages. The gaskets for insertion in the ferrule 200 will generally be annular and may be either standard or as illustrated in FIG. 4 or 5.

Figure 4A:
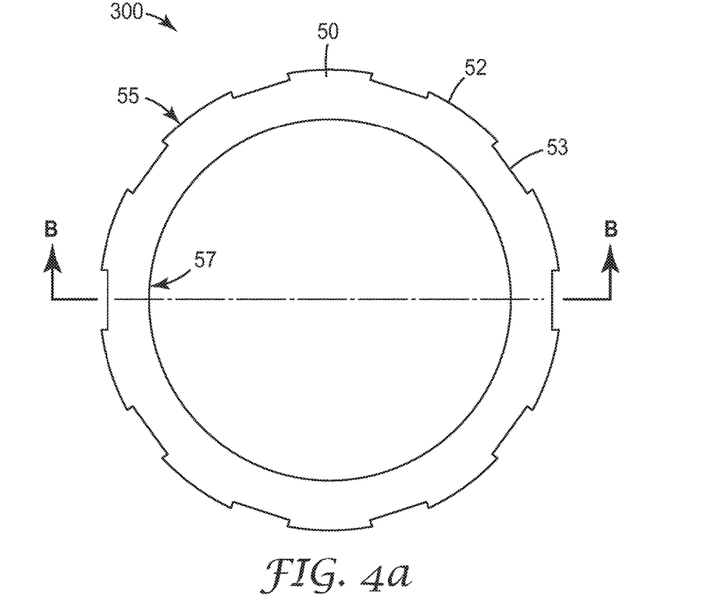
FIG. 4a shows a plan view of a first embodiment of a gasket for incorporation in valve assemblies of the invention.
Figure 4B:
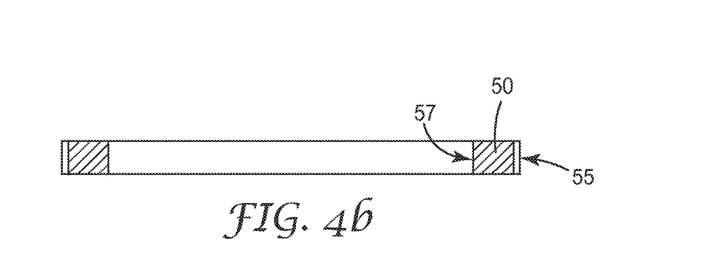

FIGS. 4a and 4b illustrate a first embodiment of a castellated gasket 300 for use in a valve according to the invention. The gasket 300 is of generally annular form and the gasket material 50 is of ethylene propylene diene monomer (EPDM) although other elastomers with appropriate properties are also suitable. The inner surface of the gasket will form a gasket inner interference surface 57 and the outer surface of the gasket will form a gasket outer interference surface 55 when inserted into a ferrule. The ferrule (not shown in FIGS. 4a and 4b) may be either standard or may be shaped as a castellated ferrule 200 (e.g. as shown in FIG. 3), in accordance with the present specification. The outer interference surface 55 has ten evenly spaced cut outs 53 of generally rectangular profile separated by protrusions 52 around its circumference. The cut outs 53 surprisingly improve retention of the gasket in the ferrule with important production advantages.

Figure 5A:
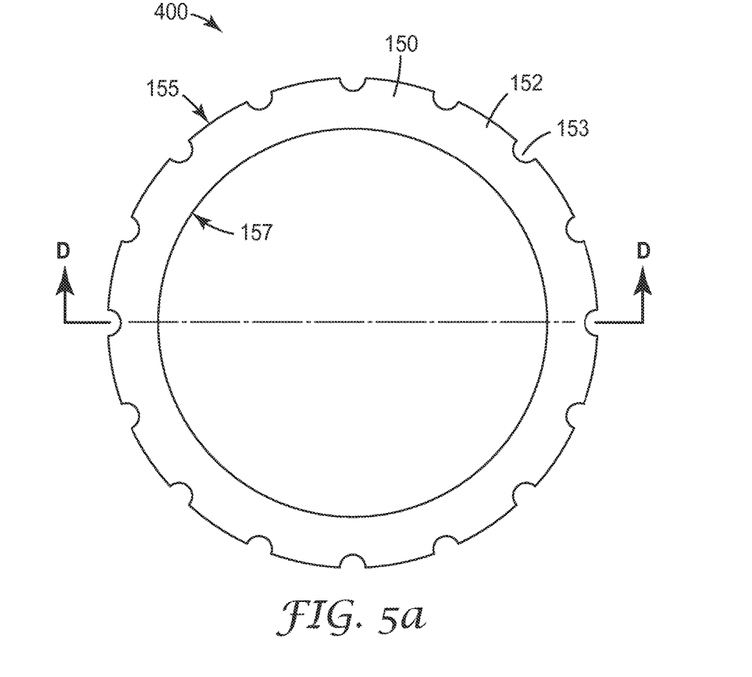
FIG. 5a shows a plan view of a second embodiment of a gasket for incorporation in valve assemblies of the invention.
Figure 5B:
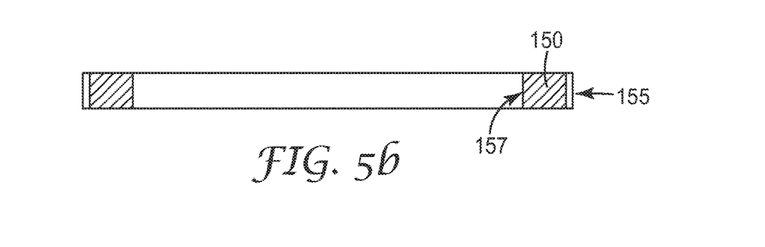

FIGS. 5a and 5b illustrate a second embodiment of a pecked gasket 400 for use in a valve according to the invention. The gasket 400 is of generally annular form and the gasket material 150 is of ethylene propylene diene monomer (EPDM) although other elastomers with appropriate properties are also suitable. The inner surface of the gasket will form a gasket inner interference surface 157 and the outer surface of the gasket will form a gasket outer interference surface 155 when inserted into a ferrule. The ferrule (not shown in FIGS. 5a and 5b) may be either standard or may be shaped as a castellated ferrule 200 (e.g. as shown in FIG. 3), in accordance with the present specification. The outer interference surface 155 has sixteen evenly spaced cut outs 153 of generally semi-circular profile separated by protrusions 152 around its circumference. The cut outs 153, as in the castellated gasket embodiment of FIG. 4, surprisingly improve retention of the gasket in the ferrule with important production advantages.

EXAMPLES

In the Examples, various ferrule/gasket sub-assemblies are assessed. The castellated ferrule as illustrated in FIG. 3 was compared to a control ferrule, and pecked gaskets as illustrated in FIG. 5 were compared with a control gasket without the cut-outs and hence with no relief pockets.

Assembly of the Valves

Ferrule plus gasket subassemblies for valves of the type illustrated in FIGS. 1 and 2 were assembled on a Haumiller production scale gasket insertion machine, which takes ferrules from a bowl feeder and in each one forces a gasket in place inside a groove designed to receive the gasket in the ferrule. The ferrule plus gasket subassemblies were inspected for gasket lifting immediately after assembly, i.e. for gaskets that were not properly located within ferrule grooves.

Subsequently, assembled valves were circulated in a bowl feeder, normally used to supply components for valve assembly, for 1 hour±10 minutes. The circulation vibrates the valves and simulates the condition during aerosol filling when the valves are made ready for crimping onto aerosol vials. Valves were then inspected for gasket lifting.

Gasket Lifting Criteria

In the ensuing tables, levels were used to characterise the gasket lifting as follows:

Level 1 No lifting or creasing.
Level 1A No lifting or creasing, but the gasket inside diameter edge sits proud of the ferrule recess diameter.
Level 2 Creasing/slight lifting of the gasket, with the metal of the recess not visible underneath.
Level 3 Lifted gasket with the metal of the recess visible underneath.
Level 4 Missing gasket Measurement of the Gasket Push Fit Force The force was measured on a Lloyd Instruments LRX Tensile/Compression Tester, fitted with a 1 kN load cell. A solid steel cylinder was manufactured to a diameter to just move freely within the outer interference surface of ferrules of valves to be tested. The cylinder was screwed into the load cell. A steel base was prepared with a central hole to accommodate the nose of the ferrule and valve stem, such that when a valve was inserted valve-down, the annular part of the ferrule that contains a gasket was directly supported by the base.

A valve was placed valve stem down into the central hole of the base and a gasket placed lightly in the ferrule recess region.

Figure 6:
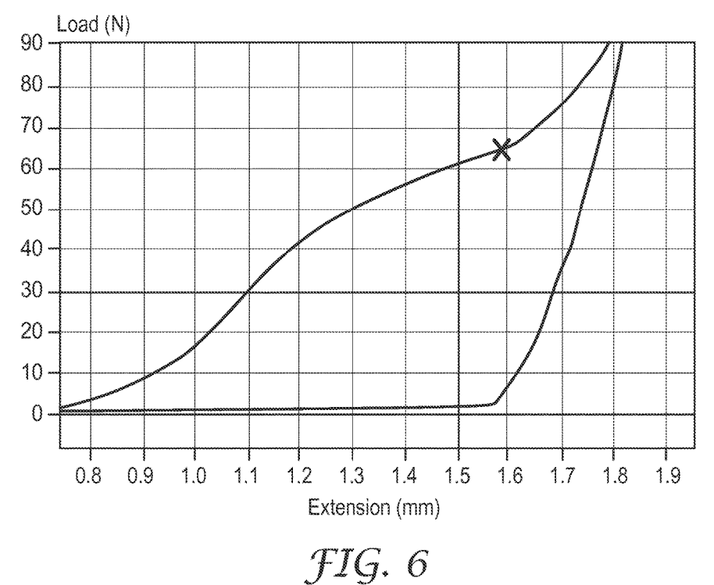
FIG. 6 is a graph of the results of a load-extension test on a J. J. Lloyd function testing machine, showing the developed force as a function of distance traveled and also the corresponding reducing force upon retraction.

The Lloyd tester was operated by programme in compression mode directing the steel cylinder at the gasket at 20 mm per minute (333 μm per s), until a force of 200N developed, whereupon the steel cylinder was retracted at 20 mm per minute (333 μm per s). A trace was produced indicating the developed force as a function of distance traveled by the steel cylinder, and the corresponding reducing force upon retraction, as illustrated in FIG. 6. The force to push fit was determined by taking the intercept of the retraction trace with the axis of zero force, then looking up the developing force corresponding to the same extension.

Example 1 Ferrule Comparison

Standard gaskets at different sizes within usual manufacturing tolerance were used, with the aim of investigating specific interference fit levels. The Mean Total Interference values were chosen to straddle the usual range of Mean Total Interference values of standard valves.

The 'Mean Total Interference' is calculated as (Gasket Mean outer interference surface diameter (x)−Ferrule Mean outer interference surface diameter (y))+(Ferrule Mean inner interference surface diameter (w)−Gasket Mean inner interference surface diameter (v)).

The recesses 38 in the Example ferrule were approximately 0.23 mm "deep" (radially) and approximately 3.00 mm "wide" (circumferentially). There were ten such recesses in each Example ferrule.

Table 1 shows the individual mean measurements and the calculated total interference. Table 2A shows the results of visual inspection immediately upon assembly. Table 2B shows the results of visual inspection after bowl feeder trials.

TABLE 1

| | | Ferrule | | Gasket | | Interference Mean |
|---|---|---|---|---|---|---|
| Lot | Description | w (mm) | y (mm) | x (mm) | v (mm) | Total (mm) |
| 1 | Control ferrule High interference | 15.761 | 19.677 | 19.812 | 15.621 | 0.275 |
| 2 | Control ferrule Low interference | 15.761 | 19.677 | 19.710 | 15.723 | 0.071 |
| 3 | Example ferrule High interference | 15.748 | 19.685 | 19.812 | 15.621 | 0.254 |
| 4 | Example ferrule Low interference | 15.756 | 19.685 | 19.710 | 15.723 | 0.058 |

TABLE 2A

| | | | Visual % (immediate post Haumiller) | | | | |
|---|---|---|---|---|---|---|---|
| Lot | Quantity | Description | Level 1 | Level 1A | Level 2 | Level 3 | Level 4 |
| 1 | 315 | Control ferrule High interference | 83.8 | 15.9 | 0.3 | 0 | 0 |
| 2 | 315 | Control ferrule Low interference | 83.8 | 0 | 14.6 | 1.6 | 0 |
| 3 | 315 | Example ferrule High interference | 100 | 0 | 0 | 0 | 0 |
| 4 | 315 | Example ferrule Low interference | 100 | 0 | 0 | 0 | 0 |

TABLE 2B

| | | | Visual % (post bowl feeder) | | | | |
|---|---|---|---|---|---|---|---|
| Lot | Quantity | Description | Level 1 | Level 1A | Level 2 | Level 3 | Level 4 |
| 1 | 315 | Control ferrule High interference | 73.3 | 26.4 | 0.3 | 0 | 0 |
| 2 | 315 | Control ferrule Low interference | 78.4 | 1.6 | 16.8 | 3.2 | 0 |
| 3 | 315 | Example ferrule High interference | 100 | 0 | 0 | 0 | 0 |
| 4 | 315 | Example ferrule Low interference | 100 | 0 | 0 | 0 | 0 |

Visual inspection results for the exemplary ferrules showed excellent gasket fit results compared with controls, both immediately after assembly and after bowl feeder trials. Push fit forces are shown in Table 3.

TABLE 3

| | | Lloyd Gasket Push Fit Test: Force in Newtons | | | |
|---|---|---|---|---|---|
| Lot | Description | Min | Max | Mean | Range |
| 1 | Control ferrule High interference | 70 | 80.1 | 75.7 | 10.1 |
| 2 | Control ferrule Low interference | 51.9 | 86.6 | 65.9 | 34.7 |
| 3 | Example ferrule High interference | 29.8 | 44.5 | 37.3 | 14.7 |
| 4 | Example ferrule Low interference | 29.3 | 52.5 | 43 | 23.2 |

The forces shown in Table 3 for the exemplary valves were lower than for the controls, independently of the extent of interference.

Example 2 Gasket Comparison

Standard ferrules at different sizes within usual manufacturing tolerance were used, with the aim of investigating specific interference fit levels.

TABLE 4

| | | Ferrule | | Gasket | | Interference Mean |
|---|---|---|---|---|---|---|
| Lot | Description | w (mm) | y (mm) | x (mm) | v (mm) | Total (mm) |
| 5 | Pecked gasket Low interference | 15.718 | 19.715 | 19.685 | 15.596 | 0.092 |
| 6 | Pecked gasket High interference | 15.761 | 19.677 | 19.685 | 15.596 | 0.173 |
| 7 | Control gasket Recommended interference | 15.672 | 19.736 | 19.812 | 15.621 | 0.127 |

TABLE 5A

| | | | Visual % (immediate post Haumiller) | | | | |
|---|---|---|---|---|---|---|---|
| Lot | Quantity | Description | Level 1 | Level 1A | Level 2 | Level 3 | Level 4 |
| 5 | 112 | Pecked gasket Low interference | 99 | 1 | 0 | 0 | 0 |
| 6 | 115 | Pecked gasket High interference | 100 | 0 | 0 | 0 | 0 |
| 7 | 354 | Control gasket Recommended interference | 54.5 | 0 | 41.5 | 4.0 | 0 |

TABLE 5B

| | | | Visual % (post bowl feeder) | | | | |
|---|---|---|---|---|---|---|---|
| Lot | Quantity | Description | Level 1 | Level 1A | Level 2 | Level 3 | Level 4 |
| 5 | 112 | Pecked gasket Low interference | 99 | 1 | 0 | 0 | 0 |
| 6 | 115 | Pecked gasket High interference | 100 | 0 | 0 | 0 | 0 |
| 7 | 354 | Control gasket Recommended interference | 54.5 | 0 | 40.1 | 5.4 | 0 |

The Mean Total Interference values were chosen to straddle the usual range of Mean Total Interference values of standard valves.

The Mean Total Interference was calculated as above.

The cut outs 153 in the Example pecked gasket were approximately semi-cylindrical, with a "depth" (radially) of approximately 1.00 mm and hence an "opening width" (circumferentially) of approximately 2.00 mm. There were sixteen such cut outs in each Example pecked gasket.

Table 4 shows the individual mean measurements and the calculated Mean Total Interference. Table 5A shows the results of visual inspection immediately upon assembly.

Table 5B shows the results of visual inspection after bowl feeder trials.

Visual inspection results for the exemplary gaskets showed much improved gasket fit results compared with controls, both immediately after assembly and after bowl feeder trials. Push fit forces are shown in Table 6.

TABLE 6

| | | Lloyd Gasket Push Fit Test: Force in Newtons | | | |
|---|---|---|---|---|---|
| Lot | Description | Min | Max | Mean | Range |
| 5 | Pecked gasket Low interference | 48.9 | 60.4 | 55.7 | 11.5 |
| 6 | Pecked gasket High interference | 61.8 | 90.2 | 74.3 | 28.4 |
| 7 | Control gasket Recommended interference | 22.3 | 64.2 | 45.3 | 41.9 |

The invention claimed is:

1. A valve for an aerosol canister, the valve comprising a valve assembly, a ferrule for holding the valve assembly and a gasket for insertion into the ferrule, wherein the ferrule has at least one ferrule interference surface and the gasket has at least one gasket interference surface, and wherein the contact zone between the ferrule interference surface and the gasket interference surface comprises a plurality of relief portions, and wherein the gasket interference surface comprises a plurality of gasket relief pockets.

2. A valve as claimed in claim 1, wherein the ferrule interference surface comprises a plurality of ferrule relief pockets.

3. A valve as claimed in claim 2, wherein the ferrule relief pockets are distributed substantially evenly on the ferrule interference surface.

4. A valve as claimed in claim 1 wherein the ferrule interference surface and/or the gasket interference surface comprise five or more relief portions or relief pockets.

5. A valve as claimed in claim 1, wherein the gasket interference surface is substantially cylindrical.

6. A valve as claimed in claim 1, wherein the gasket relief pockets are distributed substantially evenly on the gasket interference surface.

7. A valve as claimed in claim 1, wherein the ferrule interference surface is substantially cylindrical.

8. A valve as claimed in claim 1, wherein the valve is a metered dose aerosol valve.

9. A valve as claimed in claim 1, wherein the valve is adapted for fitting to an aerosol container and wherein the gasket is for sealing the aerosol container.

10. A valve as claimed in claim 1, wherein the valve assembly comprises a helical spring, a seal and a valve stem, the valve stem and seal being in mutual sliding sealing engagement, the helical spring comprising a coil of elongate material for returning the valve stem to a rest position.

11. A valve as claimed in claim 10, wherein the ferrule relief pockets are recessed by between 0.1 and 1.5 mm.

12. A valve as claimed in claim 10, wherein the gasket relief pockets are recessed by between 0.02 and 2.5 mm.

13. A valve as claimed in claim 1 wherein the relief pockets are recesses in the gasket interference surface or ferrule interference surface.

14. An aerosol container having fitted thereto a valve as claimed in claim 1.

15. A valve for an aerosol canister, the valve comprising a valve assembly, a ferrule for holding the valve assembly and a gasket for insertion into the ferrule, wherein the ferrule has at least one ferrule interference surface and the gasket has at least one gasket interference surface, and wherein the ferrule interference surface and/or the gasket interference surface comprise a plurality of relief pockets, and wherein the gasket interference surfaces comprises a plurality of gasket relief pockets.

16. A valve as claimed in claim 15 wherein the ferrule interference surface and/or the gasket interference surface comprise five or more relief portions or relief pockets.

17. A valve as claimed in claim 15, wherein the gasket interference surface is substantially cylindrical.

18. A valve as claimed in claim 15, wherein the gasket relief pockets are distributed substantially evenly on the gasket interference surface.

19. A valve as claimed in claim 15, wherein the ferrule interference surface is substantially cylindrical.

20. A valve as claimed in claim 15, wherein the valve is a metered dose aerosol valve.

21. A valve as claimed in claim 15, wherein the valve is adapted for fitting to an aerosol container and wherein the gasket is for sealing the aerosol container.

22. A valve as claimed in claim 15, wherein the valve assembly comprises a helical spring, a seal and a valve stem, the valve stem and seal being in mutual sliding sealing engagement, the helical spring comprising a coil of elongate material for returning the valve stem to a rest position.

23. A valve as claimed in claim 22, wherein the ferrule relief pockets are recessed by between 0.1 and 1.5 mm.

24. A valve as claimed in claim 22, wherein the gasket relief pockets are recessed by between 0.02 and 2.5 mm.

25. A valve as claimed in claim 15, wherein the relief pockets are recesses in the gasket interference surface or ferrule interference surface.

26. An aerosol container having fitted thereto a valve as claimed in claim 15.

27. A method of manufacturing a valve for an aerosol canister, the valve comprising a valve assembly, a ferrule for holding the valve assembly and a gasket for insertion into the ferrule, the method comprising:
providing a ferrule,
providing a gasket adapted to fit the ferrule,
inserting the gasket in the ferrule,
wherein the ferrule has at least one ferrule interference surface and the gasket has at least one gasket interference surface, and wherein the contact zone between the ferrule interference surface and the gasket interference surface comprises a plurality of relief portions, and wherein the gasket interference surface comprises a plurality of gasket relief pockets.

28. A method as claimed in claim 27, wherein the ferrule interference surface and/or the gasket interference surface comprise a plurality of relief pockets.

* * * * *

UNITED STATES PATENT AND TRADEMARK OFFICE
CERTIFICATE OF CORRECTION

PATENT NO. : 10,272,214 B2
APPLICATION NO. : 14/899020
DATED : April 30, 2019
INVENTOR(S) : Andrew Child et al.

Page 1 of 1

It is certified that error appears in the above-identified patent and that said Letters Patent is hereby corrected as shown below:

In the Specification

Column 4
Line 7, delete "terfenetate," and insert -- trifenatate, --, therefor.
Line 46, delete "4a" and insert -- 4a. --, therefor.

Signed and Sealed this
Third Day of September, 2019

Andrei Iancu
*Director of the United States Patent and Trademark Office*